(12) United States Patent
Mallet et al.

(10) Patent No.: US 12,018,000 B2
(45) Date of Patent: Jun. 25, 2024

(54) LITHIUM SALTS OF CYANO-SUBSTITUTED IMIDAZOLE FOR LITHIUM ION BATTERIES

(71) Applicants: HYDRO-QUÉBEC, Montréal (CA); MURATA MANUFACTURING CO., LTD., Nagaokakyo (JP)

(72) Inventors: Charlotte Mallet, Montreal (CA); Sylviane Rochon, Saint-Adelphe (CA); Antoine Lafleur-Lambert, Québec (CA); Shinichi Uesaka, Nagaokakyo (JP); Karim Zaghib, Longueuil (CA)

(73) Assignees: HYDRO-QUÉBEC, Montreal (CA); MURATA MANUFACTURING CO., LTD., Nagaokakyo (JP)

( * ) Notice: Subject to any disclaimer, the term of this patent is extended or adjusted under 35 U.S.C. 154(b) by 171 days.

(21) Appl. No.: 16/494,435

(22) PCT Filed: Mar. 27, 2018

(86) PCT No.: PCT/CA2018/050370
§ 371 (c)(1),
(2) Date: Sep. 16, 2019

(87) PCT Pub. No.: WO2018/176134
PCT Pub. Date: Oct. 4, 2018

(65) Prior Publication Data
US 2020/0087262 A1    Mar. 19, 2020

Related U.S. Application Data

(60) Provisional application No. 62/477,161, filed on Mar. 27, 2017.

(51) Int. Cl.
| | | |
|---|---|---|
| *C07D 233/90* | (2006.01) | |
| *C07C 311/51* | (2006.01) | |
| *C07D 207/448* | (2006.01) | |
| *C07D 233/72* | (2006.01) | |
| *C07D 233/96* | (2006.01) | |
| *H01M 4/60* | (2006.01) | |
| *H01M 4/62* | (2006.01) | |
| *H01M 10/0525* | (2010.01) | |
| *H01M 10/0567* | (2010.01) | |
| *H01M 10/0569* | (2010.01) | |

(52) U.S. Cl.
CPC .......... *C07D 233/90* (2013.01); *C07C 311/51* (2013.01); *C07D 207/448* (2013.01); *C07D 233/72* (2013.01); *C07D 233/96* (2013.01); *H01M 4/60* (2013.01); *H01M 4/62* (2013.01); *H01M 10/0525* (2013.01); *H01M 10/0567* (2013.01); *H01M 10/0569* (2013.01)

(58) Field of Classification Search
CPC .. C07D 233/72; C07D 233/90; C07D 233/96; C07D 207/448; C07C 311/51; H01M 4/60; H01M 4/62; H01M 10/0525; H01M 10/0567; H01M 10/0569
USPC ........................................ 429/304, 321, 322
See application file for complete search history.

(56) References Cited

U.S. PATENT DOCUMENTS

| | | |
|---|---|---|
| 3,637,845 A | 1/1972 | Moore et al. |
| 5,021,308 A | 6/1991 | Armand et al. |
| 6,319,428 B1 * | 11/2001 | Michot ................ C07C 317/04 564/96 |
| 7,625,922 B2 | 12/2009 | Niculescu-Duvaz et al. |
| 7,709,158 B1 | 5/2010 | Schlaikjer et al. |
| 7,906,235 B2 | 3/2011 | Michot et al. |
| 7,951,819 B2 | 5/2011 | Niculescu-Duvaz et al. |
| 8,299,074 B2 | 10/2012 | Ito et al. |
| 8,748,656 B2 | 6/2014 | Kong et al. |
| 8,871,754 B2 | 10/2014 | Chatterjee et al. |
| 9,079,893 B2 | 7/2015 | Cass et al. |
| 9,186,361 B2 | 11/2015 | Chatterjee et al. |
| 9,227,980 B2 | 1/2016 | Scherman et al. |
| 9,233,961 B2 | 1/2016 | Chatterjee et al. |
| 9,296,754 B2 | 3/2016 | Liang et al. |
| 9,303,034 B2 | 4/2016 | Biggart et al. |
| 9,439,868 B2 | 9/2016 | Scherman et al. |
| 9,926,314 B2 | 3/2018 | Chatterjee et al. |
| 9,969,687 B2 | 5/2018 | Bakthavatchalam et al. |
| 10,073,037 B2 | 9/2018 | Taylor et al. |
| 10,189,955 B2 | 1/2019 | Zhang et al. |
| 10,246,480 B2 | 4/2019 | Kim et al. |
| 10,259,809 B2 | 4/2019 | Slassi et al. |
| 10,988,466 B2 | 4/2021 | Ma et al. |

(Continued)

FOREIGN PATENT DOCUMENTS

| | | |
|---|---|---|
| CA | 2194127 A1 | 6/1998 |
| CA | 2248246 C | 2/2010 |

(Continued)

OTHER PUBLICATIONS

Sugano et al., Magnetism in organic radical ion salts based on imidazolyl and benzimidazolyl nitronyl nitroxide, 2004, Journal de Physique IV France, 114, 651-653 (Year: 2004).*
Chavez et al., Synthesis and Energetic Properties of 4,4',5,5'-Tetranitro-2,2'-biimidazolate(N4BIM) Salts, 2012, Propellants, Explosives, Pyrotechnics, 37, 647-652 (Year: 2012).*
Kircher et al., Four-Coordinate Group-14 Elements in the Formal Oxidation State of Zero-Syntheses, Structures, and Dynamics of [{(CO)$_5$Cr}$_2$Sn(L$_2$)] and Related Species, 1998, European Journal of Inorganic Chemistry, 703-720 (Year: 1998).*
Ek et al., Synthesis and Characterization of Eight Arylpentazoles, 2013, Journal of Heterocyclic Chemistry, 50, 261-267 (Year: 2013 ).*

(Continued)

*Primary Examiner* — Sean P Cullen
(74) *Attorney, Agent, or Firm* — Womble Bond Dickinson (US) LLP

(57) ABSTRACT

Here are described compounds for use as electrode additives or as salts in electrolyte compositions, and their methods of preparation. Also described are electrochemical cells comprising the compounds as electrode additives or as salts in electrolyte compositions.

22 Claims, No Drawings

(56) References Cited

U.S. PATENT DOCUMENTS

| | | | |
|---|---|---|---|
| 11,241,431 B2 | 2/2022 | Fretz et al. | |
| 11,319,299 B2 | 5/2022 | Al-Awar et al. | |
| 11,325,899 B2 | 5/2022 | Boss et al. | |
| 11,491,227 B2 | 11/2022 | Scherman et al. | |
| 2002/0102380 A1* | 8/2002 | Michot | C09B 69/02 428/64.8 |
| 2003/0096163 A1 | 5/2003 | Miyake et al. | |
| 2004/0170890 A1 | 9/2004 | Matsunaga et al. | |
| 2004/0191629 A1 | 9/2004 | Itya et al. | |
| 2004/0241543 A1 | 12/2004 | Miyake et al. | |
| 2005/0019655 A1 | 1/2005 | Miyake et al. | |
| 2005/0197450 A1 | 9/2005 | Amano et al. | |
| 2005/0266238 A1 | 12/2005 | Amano et al. | |
| 2006/0094882 A1 | 5/2006 | Umemoto | |
| 2007/0119302 A1 | 5/2007 | Ratodz et al. | |
| 2008/0176779 A1 | 7/2008 | Matsunaga et al. | |
| 2008/0255387 A1 | 10/2008 | Masaki et al. | |
| 2008/0255388 A1 | 10/2008 | Masaki et al. | |
| 2009/0032105 A1 | 2/2009 | Inoue et al. | |
| 2011/0151317 A1 | 6/2011 | Giroud et al. | |
| 2011/0206979 A1 | 8/2011 | Giroud et al. | |
| 2011/0229769 A1 | 9/2011 | Ihara et al. | |
| 2011/0311884 A1 | 12/2011 | Armand et al. | |
| 2012/0107726 A1 | 5/2012 | Ogata et al. | |
| 2013/0252112 A1 | 9/2013 | Doe et al. | |
| 2013/0310495 A1 | 11/2013 | Kim et al. | |
| 2014/0243288 A1* | 8/2014 | Zhang | C07F 9/6561 514/80 |
| 2015/0315155 A1 | 11/2015 | Armand et al. | |
| 2016/0197349 A1 | 7/2016 | Schmidt | |
| 2017/0040632 A1 | 2/2017 | Ogata et al. | |
| 2017/0040640 A1 | 2/2017 | Schmidt et al. | |

FOREIGN PATENT DOCUMENTS

| | | |
|---|---|---|
| CA | 2925554 A1 | 4/2015 |
| CN | 102760574 A | 10/2012 |
| CN | 102760576 A | 10/2012 |
| CN | 102760577 A | 10/2012 |
| CN | 102760578 A | 10/2012 |
| CN | 102956360 A | 3/2013 |
| CN | 103377834 A | 10/2013 |
| CN | 103377836 A | 10/2013 |
| CN | 103451717 A | 12/2013 |
| EP | 93915 A * 11/1983 | C07C 205/42 |
| EP | 0 412 849 A2 | 2/1991 |
| FR | 2606217 A1 | 5/1988 |
| FR | 2933814 A1 | 1/2010 |
| FR | 2935547 A1 | 3/2010 |
| JP | H 03 083981 A | 4/1991 |
| JP | H03196047 A | 8/1991 |
| JP | H11-92446 A | 4/1999 |
| JP | 2000 508676 A | 7/2000 |
| JP | H03179360 A | 6/2001 |
| JP | 2002075443 A | 3/2002 |
| JP | 2002373712 A | 12/2002 |
| JP | 2004006215 A | 1/2004 |
| JP | 2004123602 A | 4/2004 |
| JP | 2004203763 A | 7/2004 |
| JP | 2004269491 A | 9/2004 |
| JP | 2005104845 A | 4/2005 |
| JP | 2005104846 A | 4/2005 |
| JP | 2005139100 A | 6/2005 |
| JP | 2005158880 A | 6/2005 |
| JP | 2005183195 A | 7/2005 |
| JP | 2005350579 A | 12/2005 |
| JP | 2006052362 A | 2/2006 |
| JP | 2006063274 A | 3/2006 |
| JP | 2006206457 A | 8/2006 |
| JP | 2006206458 A | 8/2006 |
| JP | 2006210022 A | 8/2006 |
| JP | 2006210817 A | 8/2006 |
| JP | 2006347938 A | 12/2006 |
| JP | 2007016007 A | 1/2007 |
| JP | 2007-051067 A | 3/2007 |
| JP | 2007051241 A | 3/2007 |
| JP | 2008260899 A | 10/2008 |
| JP | 2009117168 A | 5/2009 |
| JP | 2009179671 A | 8/2009 |
| JP | 2011203644 A | 10/2011 |
| JP | 2011225764 A | 11/2011 |
| JP | 2012 500833 A | 1/2012 |
| JP | 2012126877 A | 7/2012 |
| JP | 2013060551 A | 4/2013 |
| JP | 2013084668 A | 5/2013 |
| JP | 2013129785 A | 7/2013 |
| JP | 2013196878 A | 9/2013 |
| JP | 2013196922 A | 9/2013 |
| JP | 2014-007117 A | 1/2014 |
| JP | 2014-096213 A | 5/2014 |
| JP | 2014096290 A | 5/2014 |
| JP | 2014194866 A | 10/2014 |
| JP | 2015038870 A | 2/2015 |
| JP | 2015108098 A | 6/2015 |
| JP | 2015118267 A | 6/2015 |
| JP | 2015194521 A | 11/2015 |
| JP | 2016045441 A | 4/2016 |
| JP | 2016118619 A | 6/2016 |
| JP | 2016 532275 A | 10/2016 |
| JP | 2016 535917 A | 11/2016 |
| JP | 2017016011 A | 1/2017 |
| KR | 2010019661 A | 2/2010 |
| KR | 2014088642 A | 7/2014 |
| KR | 2016063505 A | 6/2016 |
| KR | 2016084765 A | 7/2016 |
| WO | 2003/012900 A1 | 2/2003 |
| WO | 2003/036751 A1 | 5/2003 |
| WO | 2003/054986 A1 | 7/2003 |
| WO | 2004/078898 A1 | 9/2004 |
| WO | 2006/095894 A1 | 9/2004 |
| WO | 2007/125845 A1 | 11/2007 |
| WO | 2006/109769 A1 | 11/2008 |
| WO | 2009/123784 A1 | 10/2009 |
| WO | 2010/004012 A2 | 1/2010 |
| WO | 2010/023185 A1 | 3/2010 |
| WO | 2010/028439 A1 | 3/2010 |
| WO | 2010023413 A1 | 3/2010 |
| WO | 2010/090253 A1 | 8/2010 |
| WO | 2010/096404 A2 | 8/2010 |
| WO | 2010/151639 A2 | 12/2010 |
| WO | WO 2011/118853 | 9/2011 |
| WO | 2013/045561 A1 | 4/2013 |
| WO | 2013/049021 A1 | 4/2013 |
| WO | 2010/113971 A1 | 2/2017 |

OTHER PUBLICATIONS

Hatzade et al., Antimicrobial/antioxidant activity and POM analyses of novel 7-o-β-D-glucopyranosyloxy-3-(4,5-disubstituted imidazol-2-yl)-4H-chromen-4-ones, 2015, Medicinal Chemistry Research, 24, 2679-2693 (Year: 2015).*

Wikipedia contributors, Heterocyclic compound, Oct. 30, 2022, Wikipedia—The Free Encyclopedia (Year: 2022).*

Extended European Search Report dated Dec. 9, 2020, issued by the European Patent Office in corresponding European Application No. 18774359.6-1110, (9 pages).

Niedzicki, L. et al."New type of imidazole based salts designed specifically for lithium ion batteries" Elecrrochimica Acra, vol. 55, 2010, pp. 1450-1454.

International Search Report (PCT/ISA/210) dated Jun. 18, 2018, by the Canadian Patent Office as the International Searching Authority for International Application No. PCT/CA2018/050370.

Written Opinion (PCT/ISA/237) dated Jun. 18, 2018, by the Canadian Patent Office as the International Searching Authority for International Application No. PCT/CA2018/050370.

Antoniotti, P. et al., "Cl-Initiated oxidation of N-ethyl-perfluoroalkanesulfonamides: A theoretical insight into the experimentally observed products" J. Molec. Structure: THEOCHEM (2008), vol. 857, pp. 57-65.

Behrend, E. et al., "Pseudohalogenverbindungen. XX*. Perfluorierte Alkan-Und Phenylsulfonylpseudohalogenide" J. Fluorine Chem. (1974), vol. 4, No. (1), pp. 83-98.

(56) References Cited

OTHER PUBLICATIONS

Burk, P. et al., "Superacidity of Neutral Bronsted Acids in Gas Phase" Journal of Computational Chemistry, (1996), vol. 17, No. (1), pp. 30-41.

Cocalia, V. et al., "Crystallization of Uranyl Salts from Dialkylimidazolium Ionic Liquids or Their Precursors" Eur. J. of Inorg. Chem. (2010), vol. 18, pp. 2760-2767.

De Luca, L. et al."An Easy Microwave-Assisted Synthesis of Sulfonamides Directly from Sulfonic Acids" J. Org. Chem. (2008), vol. 73, pp. 3967-3969.

Erdni-Goryaev, E.M. et al., New Membrane Materials Based on Crosslinked Poly(ethylene glycols) and Ionic Liquids for Separation of Gas Mixtures Containing $CO_2$ Polymer Science, Series B (2014), vol. 56, No. (6), pp. 900-908.

Frye, C. L. et al.,"Triptych-Siloxazolidines: Pentacoordinate Bridgehead Silanes Resulting From Transannular Interaction of Nitrogen and Silicon" J. Am. Chem. Soc., (1961), vol. 83, pp. 996-997.

Gharagheizi, F. et al., "A group contribution method for estimation of glass transition temperature ionic liquids" Chemical Engineering Science, (2012), vol. 81, pp. 91-105.

Ishida, Y. et al., "Synthesis and properties of a diastereopure ionic liquid with planar chirality" Tetrahedron Letters (2006), vol. 47, No. (45), pp. 7973-7976.

Izgorodina, E. I. et al., "Towards a Better Understanding of 'Delocalized Charge' in Ionic Liquid Anions" Australian Journal of Chemistry, (2007), vol. 60, No. (1), pp. 15-20.

Kawanami, H. et al., "Effective $scCO_2$-ionic Liquid Reaction System Based on Symmetric Aliphatic Ammonium Salts for the Rapid $CO_2$ Fixation with Aziridine to 2-Oxazolidinone" Chemistry Letters (2005), vol. 34, No. (1), pp. 60-61.

Kimura, A. et al., "Study on the reaction of chlorophenols in room temperature ionic liquids with ionizing radiation" Radiation Physics and Chemistry, (2008), vol. 77, No (10-12), pp. 1253-1257.

Koppel, I.A. et al., "The Gas-Phase Acidities of Very Strong Neutral Bronsted Acids" J. Am. Chem. Soc. (1994), vol. 116, No. (7), pp. 3047-3057.

Ladouceur, S. et al.,"Synthesis and characterization of a new family of aryltrifluoromethanesulfonylimide Li-Salts for Li-ion batteries and beyond" J. Power Source, (2015), vol. 293, pp. 78-88.

Lazzus, Juan A., "A Group Contribution Method to Predict ρ-T-P of Ionic Liquids" Chem. Engin. Comm., (2010), vol. 197, No. (7), pp. 974-1015.

Lazzus, Juan A., :A group contribution method to predict the melting point of ionic liquids Fluid Phase Equilibria, (2012), vol. 313, pp. 1-6.

Matsumoto, H. et al., "Room temperature ionic liquids based on small aliphatic ammonium cations and asymmetric amide anions" Chem. Comm. (Cambridge, UK), (2002), vol. (16), pp. 1726-1727.

Matsumoto, H. et al., "Low Melting and Electrochemically Stable Ionic Liquids Based on Asymmetric Fluorosulfonyl(trifluoromethylsulfonyl)amide" Chem. Lett. ,(2008), vol. 37, No. (10), pp. 1020-1021.

Matsumoto, H. et al., "$Li/LiCoO_2$ Cell Performance Using Ionic Liquids Composed of N,N-Diethyl-Nmethyl-N-(2-methoxyethyl)ammonium—Effect of Anionic Structure" ECS Trans. (2009), vol. 16, No. (35), pp. 59-66.

Matsumoto, H. et al., "Preparation of room temperature ionic liquids based on aliphatic onium cations and asymmetric amide anions and their electrochemical properties as a lithium battery electrolyte" Journal of Power Sources, (2005), vol. 146, No. (1-2), pp. 45-50.

Matsumoto, H. et al., "Physical and Electrochemical Properties of Room Temperature Molten Salt Based on Aliphatic Onium Cations and Asymmetric Amide Anion" Proceedings—Electrochem. Soc. (2002), PV 2002-19, pp. 1057-1065.

Middleton, W. J. et al., "Cyanocarbon Chemistry. IV.1 Dicyanoketene Acetals"J. Am. Chem. Soc. (1958), vol. 80, pp. 2788-2795.

Mirkhani, S. A et al., "Determination of the glass transition temperature of ionic liquids: A molecular approach" Thermochimica Acta, (2012), vol. 543, pp. 88-95.

Mokadem, K. et al., "A new group-interaction contribution method to predict the thermal decomposition temperature of ionic liquids" Chemometrics and Intelligent Lab. Systems, (2016), vol. 157, pp. 189-295.

Mokadem, K. et al., "An enhanced group-interaction contribution method for the prediction of glass transition temperature of ionic liquids" Fluid Phase Equilibria, (2016), vol. 425, pp. 259-268.

Noguchi T. et al., "Cyclophane-shaped ionic liquids with planar chirality: effects of bridge unit on thermal properties and chirality-recognition ability" Tetrahedron, (2016), vol. 72, No. 11, pp. 1493-1504.

Oishi, A. et al.,"Novel styrene/N-phenylmaleimide alternating copolymers with pendant sulfonimide acid groups for polymer electrolyte fuel cell applications" Journal of Materials Chemistry, (2009), vol. 19, No. (4), pp. 514-521.

Petrik. V.N. et al., "N-Bis(methylthio)methylene-trifluoromethanesulfonylamide $CF_3SO_2N=C(SCH_3)_2$: new reagent for the preparation of N-trifluoromethylsulfonylimino carbonic and thiocarbonic acids derivatives" Journal of Fluorine Chemistry, (2003), vol. 124, pp. 151-158.

Pilli, S. et al., "Extraction of pentachlorophenol and dichlorodiphenyltrichloroethane from aqueous solutions using ionic liquids" J. of Ind. and Eng. Chem., (2012), vol. 18, No. (6), pp. 1983-1996.

Sakaebe, H. et al., "Application of room temperature ionic liquids to Li batteries" Electrochimica Acta, (2007), vol. 53, No. (3), pp. 1048-1054.

Sakaebe, H. et al., "Discharge-charge properties of $Li/LiCoO_2$ cell using room temperature ionic liquids (RTILs) based on quaternary ammonium cation—Effect of the structure" Journal of Power Sources, (2005), vol. 146, No. (1-2), pp. 693-697.

Shaplov, A., et al., "New family of highly conductive and low viscous ionic liquids with asymmetric 2,2,2-trifluoromethylsulfonyl-N-cyanoamide anion" Electrochimica Acta, (2015), vol. 175, pp. 254-260.

Umecky, T. et al., "Influence of Anion Structure on Transport Properties of Perfluorosulfonylamide Ionic Liquids" ECS Trans., (2009), vol. 16, No. (49), pp. 39-51.

Valderrama, J.O. et al., "Critical Properties, Normal Boiling Temperature, and Acentric Factor of Another 200 Ionic Liquids" Ind. & Eng. Chemistry Research (2008), vol. 47, No. (4), pp. 1318-1330.

Venkatasetty, H. V. et al.,"Recent Advances in Lithium-Ion and Lithium-Polymer Batteries" Annual Battery Conference on Applications and Advances, 17th, Long Beach, CA, U. S., Jan. 15-18, 2002, pp. 173-178.

Venkatasetty, H. V., "New and Novel Lithium Imide Electrolytes and Copolymers: Synthesis and Characterization for Lithium Rechargeable Batteries" Annual Battery Conference on Applications and Advances, 16th, Long Beach, CA, U. S., Jan. 9-12, 2001, 277-282.

Yasuda, T. et al., "Alternating Copolymer Based on Sulfonamide-Substituted Phenylmaleimide and Vinyl Monomers as Polymer Electrolyte Membrane" J. of Polym. Sc., Part A: Polym. Chem., (2013), vol. 51, No. (10), pp. 2233-2242.

Ye, F. et al.,"Preparation of fluorinated imides" Journal of Fluorine Chemistry, (1997), vol. 81, No. (2), pp. 193-196.

Ye, F. et al., "Preparation and properties of conducting polypyrrole doped with fluorinated imides" Synthetic Metals, (1993), vol. 60, No. (2), pp. 141-144.

Zhu, S. et al., "Reactions of fluorine-containing N-sulfinylamides with carboxylic acids and acid anhydrides" Journal of Fluorine Chemistry, (1995), vol. 74, (2), pp. 203-206.

Matsumoto, H., 3. "Transport Properties of Ionic Liquids—From the Viewpoint of Walden's Law," Electrochemistry, Aug. 5, 2012, vol. 80, No. 8, pp. 591-595, Electrochemical Society of Japan, JP, English-language document (5 pages) and English-language machine translation thereof (26 pages).

Office Action (Notice of Reasons for Refusal) dated Feb. 28, 2022, by the Japanese Patent Office in corresponding Japanese Patent Application No. 2019-552897, and an English Translation of the Office Action. (9 pages).

Ek, S, et al."Synthesis and Characterization of Eight Arylpentazoles" Journal of Heterocyclic Chem., vol. 50, Mar. 2013, pp. 261-267.

(56) References Cited

OTHER PUBLICATIONS

Klapotke, T. M. et al."Energetic Derivatives of 4,4',5,5'-Tetranitro-2,2'-bisimidazole (TNBI)" Journal of Inorganic and General Chemistry, 2012, vol. 638, No. 9, pp. 1278-1286.

Kircher, P. et al."Four-Coordinate Group-14 Elements in the Formal Oxidation State of Zero-Syntheses, Structures, and Dynamics of [{(C0)5Cr}2Sn(L2)I and Related Species" European Journal of Inorganic Chemistry, Feb. 2, 1998, pp. 703-720.

Bailie et al., "Effects of C5-heterocyclic compounds on CO adsorption and crotonaldehyde hydrogenation over supported Cu and Co catalysts", Physical Chemistry Chemical Physics, 2000, vol. 2, p. 283-290.

Chen et al., "Fluorocarbon and Hydrocarbon N-Heterocyclic (C5-C7) Imidazole-Based Liquid Crystals", Chemistry an Asian Journal, 2014, vol. 9, p. 3418-3430.

Declaration of Charlotte Mallet, Jul. 7, 2023.
Declaration of Jean-Christophe Daigle, Jul. 7, 2023.

\* cited by examiner

LITHIUM SALTS OF CYANO-SUBSTITUTED IMIDAZOLE FOR LITHIUM ION BATTERIES

RELATED APPLICATION

This application claims priority to U.S. provisional application No. 62/477,161 filed on Mar. 27, 2017, the content of which is incorporated herein by reference in its entirety for all purposes.

TECHNICAL FIELD

The technical field generally relates to salts for use in electrolyte compositions or as additive in electrode material, and to methods for the preparation. The technical field also relates to electrolyte compositions and electrode materials containing such salts and to batteries containing them.

BACKGROUND

Battery electrolytes, being either liquid, gel or solid, generally consists in one or more lithium salts dissolved in a solvent and/or a solvating polymer. Additives may also further be added to improve the electrolyte's properties, e.g. its stability.

Some of these salts may also be included in an electrode material to improve ionic conductivity of the material. Among the salts generally used, $LiPF_6$ (lithium hexafluorophosphate) possesses interesting properties, but degrades in the presence of water to form hydrofluoric acid (HF). This HF formed may result in a dissolution of the cathode material.

Other salts were also developed, including LiFSI and LiTFSI as well as LiTDI. These salts also have their own drawbacks. For example, the $TFSI^-$ anion is very reactive and often leads to the corrosion of the aluminum current collector even at low voltage. Both LiFSI and LiTFSI are not recommended for high voltage applications and are expensive. LiTDI is more stable than the other two but is very hygroscopic and has conductivity and solubility issues.

Therefore, it is highly desirable to develop new salts for use in electrolyte compositions or as additives in electrode materials, for instance, having one or more of the following advantages compared to currently used salts: improved ionic conductivity, lower production costs, improved solubility in electrolyte solvents, and/or the formation of a more conductive SEI.

SUMMARY

According to one aspect, here is described a compound, for instance a salt, for use in electrolyte compositions and/or as additive in electrode materials. In one embodiment, the compound is as defined in Formula I:

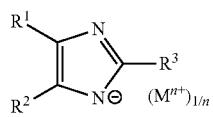

Formula I wherein,
$R^1$ and $R^2$ are independently selected from H, F, CN, $NO_2$, optionally substituted alkyl, preferably CN;

$R^3$ is selected from $NHSO_2R^4$, $NHSO_2OR^4$, $SO_2NHSO_2R^4$, $SO_2NHSO_2OR^4$ or an optionally substituted heterocycle;

$R^4$ is selected from fluorine, optionally substituted $C_{1-6}$alkyl, and optionally substituted $C_6$aryl;

$(M^{n+})_{1/n}$ is a metal cation, wherein M is a metal and n is 1 or 2, for instance M is an alkali metal, alkaline earth metal, for instance, M is Li, Na, or K, or M is Li and n is 1;

or a tautomer thereof.

In one embodiment, $R^3$ is $NHSO_2R^4$. In another embodiment, $R^3$ is $NHSO_2OR^4$. For instance, $R^4$ is a $C_{1-6}$alkyl substituted with at least one of fluorine and alkoxy, or $R^4$ is a $C_6$aryl substituted with at least one fluorine atom. In another embodiment, $R^3$ is a heterocycle. In another embodiment, at least one of $R^1$ and $R^2$ is CN, or both of $R^1$ and $R^2$ are CN.

In a further embodiment, the compound of Formula I is compound is selected from:

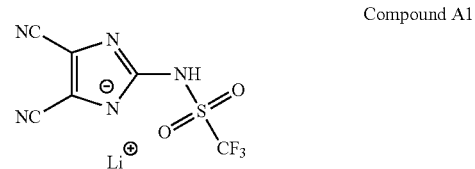

Compound A1

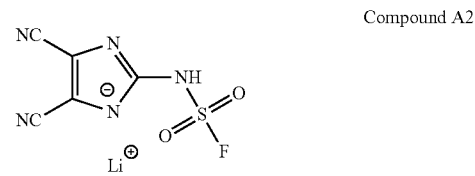

Compound A2

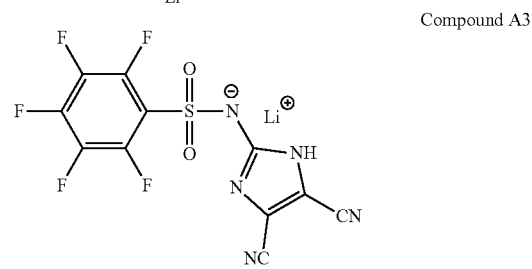

Compound A3

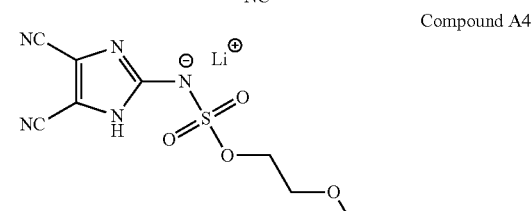

Compound A4

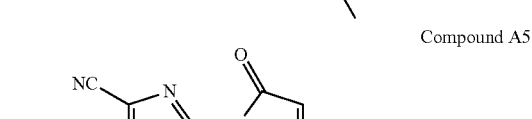

Compound A5 or a tautomer thereof.

According to another embodiment, the compound is as defined in Formula II:

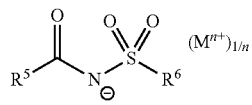

Formula II wherein,

R⁵ is selected from optionally substituted $C_{1-6}$alkyl and optionally substituted $C_6$aryl; and R⁶ is selected from optionally substituted $C_{1-6}$alkyl and optionally substituted $C_6$aryl;

$(M^{n+})_{1/n}$ is a metal cation, wherein M is a metal and n is 1 or 2, for instance M is an alkali metal, alkaline earth metal, for instance, M is Li, Na, or K, or M is Li and n is 1;

or a tautomer thereof.

In one embodiment, R⁵ is an unsubstituted $C_{1-6}$alkyl group. In another embodiment, R⁵ is a fluorinated $C_{1-6}$alkyl group. In a further embodiment, R⁶ is a fluorinated $C_{1-6}$alkyl group. In yet another embodiment, R⁶ is a fluorinated $C_6$aryl group. In yet another embodiment, at least one of R⁵ and R⁶ is an optionally substituted $C_6$aryl group (e.g. a $C_6$aryl group substituted with one or more fluorine atoms). In other embodiments, the compound is of Formula II, provided that when R⁶ is trifluoromethyl, then R⁵ is other than methyl or trifluoromethyl.

In a further embodiment, the compound of Formula II is compound is selected from:

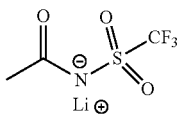

Compound B1

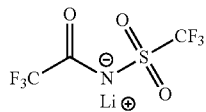

Compound B2

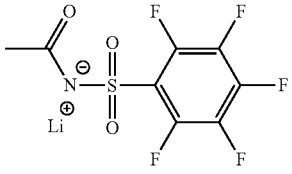

Compound B3

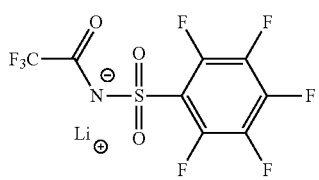

Compound B4 or a tautomer thereof.

According to a further embodiment, the compound is as defined in Formula III:

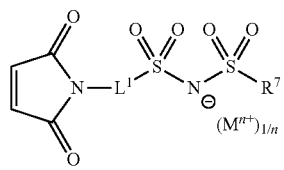

Formula III wherein,

R⁷ is selected from a fluorine atom and optionally substituted $C_{1-6}$alkyl; and L¹ is a covalent bond or a linker selected from optionally substituted $C_{1-6}$ alkyl and optionally substituted $C_6$aryl;

$(M^{n+})_{1/n}$ is a metal cation, wherein M is a metal and n is 1 or 2, for instance M is an alkali metal, alkaline earth metal, for instance, M is Li, Na, or K, or M is Li and n is 1;

or a tautomer thereof.

In one embodiment, R⁷ is a fluorine atom. In another embodiment, R⁷ is selected from fluorine substituted $C_{1-6}$alkyl groups. In a further embodiment, L¹ is a covalent bond or L¹ is a linker selected from optionally substituted $C_6$aryl groups.

In a further embodiment, the compound of Formula III is compound is selected from:

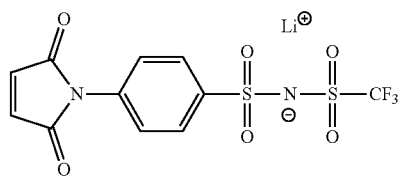

Compound C1

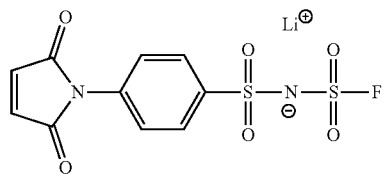

Compound C2

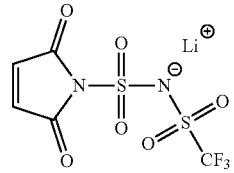

Compound C3

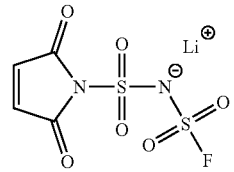

Compound C4 or a tautomer thereof.

According to another embodiment, the compound is as defined in Formula IV:

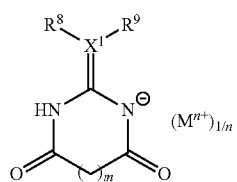

Formula IV wherein,

X¹ is a carbon or nitrogen atom;

R⁸ and R⁹ are each independently F, CN or optionally substituted $C_{1-6}$alkyl when X¹ is a carbon atom; or R⁸ is absent and R⁹ is an optionally substituted $SO_2$Alkyl or optionally substituted $C_{1-6}$alkyl when X¹ is a nitrogen atom;

$(M^{n+})_{1/n}$ is a metal cation, wherein M is a metal and n is 1 or 2, for instance M is an alkali metal, alkaline earth metal, for instance, M is Li, Na, or K, or M is Li and n is 1;

m is an integer selected from 0 or 1;

or a tautomer thereof.

In one embodiment, X¹ is a carbon atom. In one embodiment, R⁸ and R⁹ are different. Alternatively, R⁸ and R⁹ are the same. In another embodiment, at least one of R⁸ and R⁹ is CN or optionally substituted $C_{1-6}$alkyl. In one embodiment, R⁸ and R⁹ are both CN or optionally substituted $C_{1-6}$alkyl, or R⁸ and R⁹ are both CN, or R⁸ and R⁹ are both fluorine substituted $C_{1-6}$alkyl. In another embodiment, X¹ is a nitrogen atom. For example, X¹ is a nitrogen atom and R⁹ is a fluorine substituted $SO_2$Alkyl (e.g. $SO_2CF_3$). In another embodiment, m is 0. In a further embodiment m is 1.

In a further embodiment, the compound of Formula IV is compound is selected from:

Compound D1
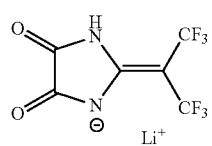

Compound D2
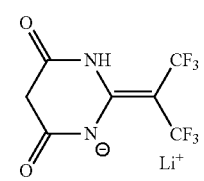

Compound D3
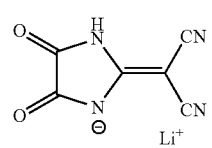

Compound D4
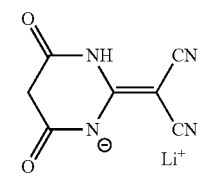

Compound D5
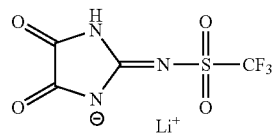

Compound D6
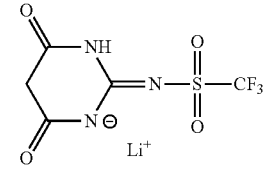

or a tautomer thereof.

According to yet another embodiment, the compound is as defined in Formula V:

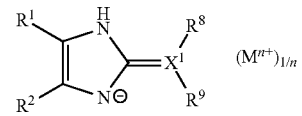

Formula V wherein, R¹, R², R⁸, R⁹, X¹, M and n are as previously defined, or R⁸ and R⁹ are absent and X¹ is an oxygen atom;

or a tautomer thereof.

In one embodiment, at least one of R¹ and R² is CN. For example, both of R¹ and R² are CN. In another embodiment, X¹ is a carbon atom. For example, X¹ is a carbon atom and R⁸ and R⁹ are both CN or optionally substituted $C_{1-6}$alkyl, or X¹ is a carbon atom and R⁸ and R⁹ are both CN, or X¹ is a carbon atom and R⁸ and R⁹ are both fluorine substituted $C_{1-6}$alkyl. In another embodiment, X¹ is a nitrogen atom. For instance, X¹ is a nitrogen atom and R⁹ is a fluorine substituted $SO_2$Alkyl (e.g. $SO_2CF_3$).

In a further embodiment, the compound of Formula V is compound is selected from:

Compound E1
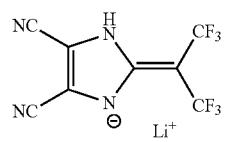

Compound E2
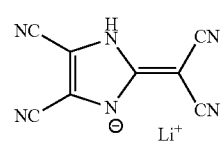

Compound E3
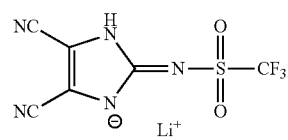

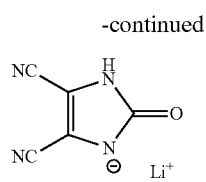

Compound E4 or a tautomer thereof.

In one embodiment, described is a compound according to any one of the foregoing embodiments, wherein M is Li and n is 1. In another embodiment, the compound is as herein defined and is a di-salt (e.g. a dianion forming a salt with two alkali metal anions, where applicable). For example, the compounds of Formulae I, IV and V, the compound may include a further anion on a second nitrogen atom. For instance, Compounds E1 to E4 may form a disalt, such as, for compound E2:

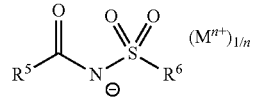

Further contemplated are the free forms of any of the salts referred to herein.

According to another aspect, the present technology relates to an electrode material comprising, as an additive, a compound as herein defined, and at least one electrochemically active material.

According to another aspect, the present technology relates to an electrolyte composition comprising a compound as herein described. For instance, the electrolyte composition further comprises a compatible solvent. In another example, the electrolyte composition further comprises a compatible solvating polymer.

In a further aspect, also contemplated is an electrochemical cell comprising an electrolyte, an electrode and a counter-electrode, wherein at least one of the electrode or counter-electrode comprises an electrode material comprising, as an additive, a compound as herein defined, and at least one electrochemically active material. Alternatively, contemplated is an electrochemical cell which comprises an electrolyte composition comprising a compound as herein defined, an electrode and a counter-electrode. In one embodiment, the electrochemical cell comprises a compound as herein defined in an electrolyte composition and in at least one electrode material. In one embodiment, electrochemical cell is included in a battery, an electrochromic device, or a capacitor. For instance, the battery is a lithium or lithium-ion battery. In other examples, the battery is a sodium or potassium battery.

According to another aspect, described in the use of the electrochemical cell as herein defined in electrical or hybrid vehicles, or in ubiquitous IT devices.

Other features and advantages of the present technology will be better understood upon reading of the description herein below.

DETAILED DESCRIPTION

Here are described compounds (e.g. salts) intended for use as electrode material additives or as a component of an electrolyte composition. Compounds described are of one of Formulae I to V as herein defined. Exemplary compounds are also described and should not be interpreted as limiting the scope of the broader formulae.

Accordingly, the compound may be as defined in Formula I:

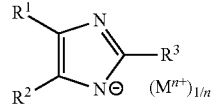

Formula I wherein, $R^1$ and $R^2$ are independently selected from H, F, CN, $NO_2$, optionally substituted alkyl, preferably CN;

$R^3$ is selected from $NHSO_2R^4$, $NHSO_2OR^4$, $SO_2NHSO_2R^4$, $SO_2NHSO_2OR^4$ or an optionally substituted heterocycle;

$R^4$ is selected from fluorine, optionally substituted $C_{1-6}$alkyl, and optionally substituted $C_6$aryl;

$(M^{n+})_{1/n}$ is a metal cation, wherein M is a metal and n is 1 or 2, for instance M is an alkali metal, alkaline earth metal, for instance, M is Li, Na, or K, or M is Li and n is 1;

or a tautomer thereof.

For example, $R^3$ is $NHSO_2R^4$, or $R^3$ is $NHSO_2OR^4$. For instance, $R^3$ is $NHSO_2R^4$ or $NHSO_2OR^4$ and $R^4$ is a $C_{1-6}$alkyl substituted with at least one of fluorine and alkoxy, or $R^4$ is a $C_6$aryl substituted with at least one fluorine atom. In another example, $R^3$ is a heterocycle having 5 or 6 cycle atoms (e.g. a non-aromatic heterocycle having 5 or 6 cycle atoms linked through a nitrogen atom, such as a maleimide). In another embodiment, at least one of $R^1$ and $R^2$ is CN, or both of $R^1$ and $R^2$ are CN.

Examples of compounds of Formula I include, without limitation, Compounds A1 to A5 as defined above, or a tautomer thereof.

The compound may also be defined as in Formula II:

Formula II wherein, $R^5$ is selected from optionally substituted $C_{1-6}$alkyl and optionally substituted $C_6$aryl; and $R^6$ is selected from optionally substituted $C_{1-6}$alkyl and optionally substituted $C_6$aryl;

$(M^{n+})_{1/n}$ is a metal cation, wherein M is a metal and n is 1 or 2, for instance M is an alkali metal, alkaline earth metal, for instance, M is Li, Na, or K, or M is Li and n is 1;

or a tautomer thereof.

For example, $R^5$ is an unsubstituted $C_{1-6}$alkyl group (such as methyl, ethyl, propyl, isopropyl and the like), or $R^5$ is a fluorinated $C_{1-6}$alkyl group (e.g. trifluoromethyl, and the like). In another example, $R^6$ is a fluorinated $C_{1-6}$alkyl group (e.g. trifluoromethyl, and the like) or $R^6$ is a fluorinated $C_6$aryl group (e.g. pentafluorophenyl, and the like). Other examples include compounds of Formula II wherein at least one of $R^5$ and $R^6$ is an optionally substituted $C_6$aryl group.

In other examples, the compound is of Formula II, provided that when $R^6$ is trifluoromethyl, then $R^5$ is other than methyl or trifluoromethyl.

Examples of compounds of Formula II include, without limitation, Compounds B1 to B4, as herein defined, or a tautomer thereof. For instance, the compound is Compounds B3 or B4, as herein defined, or a tautomer thereof.

The compound may also be as defined in Formula III:

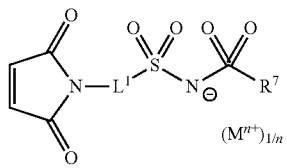

Formula III wherein,
$R^7$ is selected from a fluorine atom and optionally substituted $C_{1-6}$alkyl; and
$L^1$ is a covalent bond or a linker selected from optionally substituted $C_{1-6}$alkyl and optionally substituted $C_6$aryl;
$(M^{n+})_{1/n}$ is a metal cation, wherein M is a metal and n is 1 or 2, for instance M is an alkali metal, alkaline earth metal, for instance, M is Li, Na, or K, or M is Li and n is 1;
or a tautomer thereof.

For example, $R^7$ is a fluorine atom or $R^7$ is selected from fluorine substituted $C_{1-6}$alkyl groups. According to some examples, $L^1$ is a covalent bond. According to other examples, $L^1$ is a linker selected from optionally substituted $C_6$aryl groups.

Examples of compounds of Formula III include, without limitation, Compounds C1 to C4, as herein defined, or a tautomer thereof.

The compound may further be defined as in Formula IV:

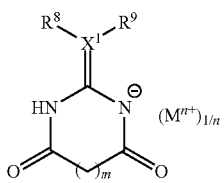

Formul IV wherein,
$X^1$ is a carbon or nitrogen atom;
$R^8$ and $R^9$ are each independently F, CN or optionally substituted $C_{1-6}$alkyl when $X^1$ is a carbon atom; or
$R^8$ is absent and $R^9$ is an optionally substituted $SO_2$Alkyl or optionally substituted $C_{1-6}$alkyl when $X^1$ is a nitrogen atom;
$(M^{n+})_{1/n}$ is a metal cation, wherein M is a metal and n is 1 or 2, for instance M is an alkali metal, alkaline earth metal, for instance, M is Li, Na, or K, or M is Li and n is 1;
m is an integer selected from 0 or 1;
or a tautomer thereof.

In some examples, $X^1$ is a carbon atom. When $X^1$ is a carbon atom, $R^8$ and $R^9$ may be the same or different. For instance, $X^1$ is a carbon atom and at least one of $R^8$ and $R^9$ is CN or optionally substituted $C_{1-6}$alkyl. For instance, $X^1$ is a carbon atom and $R^8$ and $R^9$ are both CN or optionally substituted $C_{1-6}$alkyl, or $R^8$ and $R^9$ are both CN, or $R^8$ and $R^9$ are both fluorine substituted $C_{1-6}$alkyl. According to other examples, $X^1$ is a nitrogen atom. For example, $X^1$ is a nitrogen atom, $R^8$ is absent and $R^9$ is a fluorine substituted $SO_2$Alkyl (e.g. $SO_2CF_3$). In one example, m is 0. In a further example, m is 1.

Examples of compounds of Formula IV include, without limitation, Compounds D1 to D6, as herein defined, or a tautomer thereof.

The compound may also further be defined as in Formula V:

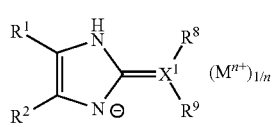

Formula V wherein, $R^1$, $R^2$, $R^8$, $R^9$, $X^1$, M and n are as previously defined, or $R^8$ and $R^9$ are absent and $X^1$ is an oxygen atom;
or a tautomer thereof.

For example, at least one of $R^1$ and $R^2$ is CN, or both of $R^1$ and $R^2$ are CN. In some examples, $X^1$ is a carbon atom. For instance, $X^1$ is a carbon atom and $R^8$ and $R^9$ are both CN or optionally substituted $C_{1-6}$alkyl, or $X^1$ is a carbon atom and $R^8$ and $R^9$ are both CN, or $X^1$ is a carbon atom and $R^8$ and $R^9$ are both fluorine substituted $C_{1-6}$alkyl. In other examples, $X^1$ is a nitrogen atom. For instance, $X^1$ is a nitrogen atom and $R^9$ is a fluorine substituted $SO_2$Alkyl (e.g. $SO_2CF_3$).

Examples of compounds of Formula V include, without limitation, Compounds E1 to E4, as herein defined, or a tautomer thereof.

According to one example, the compound is as defined in any one of Formulae I to V, wherein M is Li and n is 1. In another embodiment, the compound is as herein defined and is a di-salt (e.g. a dianion forming a salt with two alkali metal anions, where applicable). For example, the compounds of Formulae I, IV and V, the compound may include a further anion on a second nitrogen atom. Further contemplated are the free forms of any of the salts referred to herein.

As used herein, the term "alkyl" refers to saturated hydrocarbons having from one to sixteen carbon atoms, including linear or branched alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, and the like. When the alkyl group is located between two functional groups, then the term alkyl also encompasses alkylene groups such as methylene, ethylene, propylene, and the like. The term "$C_1$-$C_n$alkyl" refers to an alkyl group having from 1 to the indicated "n" number of carbon atoms.

The term "alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like.

Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as halogenated alkyloxy groups.

The term "aryl" refers to aromatic groups having 4n+2 π(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenethyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthrenyl, anthracenyl, and the like. The term aryl includes both unsubstituted aryl groups and substituted aryl groups. The term "$C_6$-$C_n$aryl" refers to an aryl group having from 6 to the indicated "n" number of carbons in the ring structure.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "substituted", when in association with any of the foregoing groups refers to a group substituted at one or more position with substituents such as cyano, halogen, nitro, trifluoromethyl, lower alkyl, cycloalkyl, heterocycloalkyl, aryl, heteroaryl, lower alkoxy, aryloxy, benzyloxy, benzyl, sulfonyl, sulfonate, sulfonamide, phosphonato, phosphinato, oxo, and the like. Any of the above substituents can be further substituted if permissible, e.g. if the group contains an alkyl group, an alkoxy group, or an aryl group.

Also described is an electrode material comprising, as an additive, a compound as herein defined, and at least one electrochemically active material. The electrochemically active material may be a material for use in a negative electrode. Alternatively, the electrochemically active material may be a material for use in a positive electrode. Examples of electrochemically active materials include, without limitation, titanates and lithium titanates (e.g. $TiO_2$, $Li_2TiO_3$, $Li_4Ti_5O_{12}$, $H_2Ti_5O_{11}$, $H_2Ti_4O_9$, or a combination thereof), lithium and metal phosphates (e.g. $LiM'PO_4$ where M' is Fe, Ni, Mn, Co, or a combination thereof), vanadium oxides (e.g. $LiV_3O_8$, $V_2O_5$, $LiV_2O_5$, and the like), and other lithium and metal oxides such as $LiMn_2O_4$, $LiM''O_2$ (M" being Mn, Co, Ni, or a combination thereof), $Li(NiM''')O_2$ (M''' being Mn, Co, Al, Fe, Cr, Ti, Zr, and the like, or a combination thereof), or a combination thereof. For instance, the active material is selected from Lithium iron phosphate (LFP), lithium manganese iron phosphate (LMFP), lithium titanate (LTO), graphite, and lithium nickel manganese cobalt oxide (NMC). The particles may be freshly formed or of commercial source, in the form of microparticles or nanoparticles and may further include a carbon coating.

The electrode material may also optionally include additional components like conductive materials, inorganic particles, glass or ceramic particles, and the like. Examples of conductive materials include carbon black, Ketjen™ black, acetylene black, graphite, graphene, carbon fibers, nanofibers (e.g. VGCF) or nanotubes, or a combination thereof. The electrode material may also further comprise a binder. Examples of binders include water soluble binders such as SBR (styrene butadiene rubber), NBR (butadiene acrylonitrile rubber), HNBR (hydrogenated NBR), CHR (epichlorohydrin rubber), ACM (acrylate rubber), and the like, and cellulose-based binders (e.g. carboxyalkylcellulose, hydroxyalkylcellulose, and combinations), or any combination of two or more of these. For instance, the carboxyalkylcellulose may be carboxymethylcellulose (CMC) or carboxyethylcellulose. Hydroxypropylcellulose is an example of hydroxyalkylcellulose. Other examples of binders include fluorine-containing polymeric binders such as PVDF and PTFE, and ion-conductive polymer binders such as block copolymers composed of at least one lithium-ion solvating segment and at least one cross-linkable segment.

According to another aspect, the present technology relates to an electrolyte composition comprising a compound as herein described. The electrolyte may be a liquid, gel or solid polymer electrolyte and, in the case of a lithium or lithium-ion electrochemical cell, is conductive to lithium ions. For instance, the electrolyte composition further comprises a compatible solvent. In another example, the electrolyte composition further comprises a compatible solvating polymer.

For example, electrolytes are prepared by dissolution of one or more of the present compounds in an appropriate electrolyte solvent or solvating polymer for polymer electrolyte preparation. For use in lithium and lithium ion batteries, the compounds as lithium salts can be dissolved at an appropriate concentration, for example between 0.05 and 3 mol/litre. For other types of batteries, other salts of the present compounds should be dissolved, for example, sodium salts for sodium batteries, magnesium salts for magnesium batteries, and the like.

Non-limiting examples of electrolyte solvents include organic solvents such as ethers, carbonate esters, cyclic carbonate esters, aliphatic carboxylic acid esters, aromatic carboxylic acid esters, phosphate esters, sulfite esters, nitriles, amides, alcohols, sulfoxides, sulfolane, nitromethane, 1,3-dimethyl-2-imidazolidinone, 1,3-dimethyl-3,4,5,6-tetrahydro-2(1,H)-pyrimidinone, 3-methyl-2-oxazolidinone, or a mixture thereof. In particular examples, the solvent may also be an aqueous solvent, i.e. water or a mixture comprising water.

Examples of solvents include dimethyl carbonate, diethyl carbonate, ethyl methyl carbonate, propylene carbonate, ethylene carbonate, γ-butyrolactone, glyme, diglyme, triglyme, tetraglyme, sulfolane, tetraethylsulfamide, acetonitrile, pyruvonitrile, propionitrile, methoxypropionitrile, dimethylaminopropionitrile, butyronitrile, isobutyronitrile, valeronitrile, pivalonitrile, isovaléronitrile, glutaronitrile, méthoxyglutaronitrile, 2-methylglutaronitrile, 3-methylglutaronitrile, adiponitrile, malononitrile, and combinations thereof. Various additives may also be included in the electrolyte composition to improve its properties.

Non-limiting examples of polymers for use in electrolytes (e.g. gel or solid) include poly(ethylene oxide) and its copolymers and block-copolymers, poly(propylene oxide) and its copolymers and block-copolymers, poly(dimethylsiloxane) and its copolymers and block-copolymers, poly(alkylene carbonate) and their copolymers and block-copolymers, poly(alkylenesulfone) and its copolymers and block-copolymers, poly(alkylenesulfamides) and its copolymers and block-copolymers, polyurethanes and their copolymers and block-copolymers, poly(vinylalcohol) and its copolymers and block-copolymers and combinations thereof. Additionally, branched or cross-linked solvating polymers may also be included. Various additives may also be included in the polymer electrolyte composition to improve its properties.

Electrochemical cells as herein described comprise an electrolyte, an electrode and a counter-electrode, wherein at least one of the electrode or counter-electrode comprises an electrode material comprising, as an additive, a compound as herein defined, and at least one electrochemically active material as defined above. Alternatively, contemplated is an electrochemical cell which comprises an electrolyte composition comprising a compound as herein defined, an electrode and a counter-electrode. In one embodiment, the electrochemical cell comprises a compound as herein defined in an electrolyte composition and in at least one electrode material. In one embodiment, the electrochemical cell is included in a battery, an electrochromic device, or a capacitor. For instance, the battery is a lithium or lithium-ion battery. In other examples, the battery is a sodium or potassium battery.

According to another aspect, described in the use of the electrochemical cell as herein defined in electrical or hybrid vehicles, or in ubiquitous IT devices.

EXAMPLES

The following non-limiting examples are illustrative embodiments and should not be construed as further limiting the scope of the present application.

Example 1: Preparation of Compounds of Formula I a) Compound A1

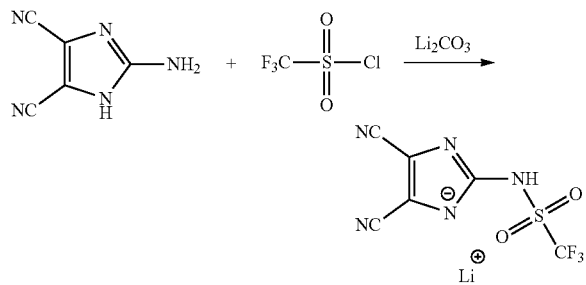

2-Amino-1H-imidazole-4,5-dicarbonitrile (1.1 eq), trifluorosulfonylchloride (1 eq), lithium carbonate (2 eq) and N'N-dimethylaminopyridine (DMAP) (0.25 eq) were introduced in a Schlenk flask. The solids were degassed by vacuum-N2 cycles. Dry acetone (1M) was added and the suspension was vigorously stirred and heated under reflux overnight. The reaction mixture was cooled down to room temperature. Distilled water was added, and the solution was extracted using dichloromethane. The combined organic layers were washed with water and acidic water, dried using MgSO4 and filtered. The solution was filtered on a diatomaceous earth filtration aid sold under the trademark CELITE® to eliminate inorganic residues. The organic solution was concentrated under reduced pressure until dryness. The solid residue was purified by silica gel chromatography using hexanes/ethyl acetate (1/1) as eluent. A crystalline yellow solid was isolated after evaporation. This yellow solid was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

b) Compound A2

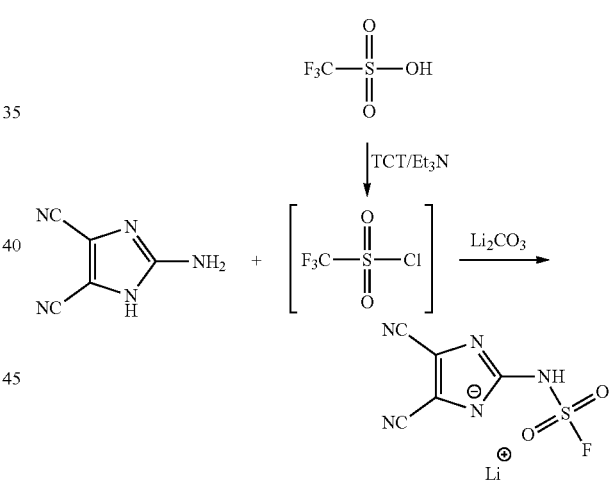

2,4,6-Trichloro-[1,3,5]-triazine (1 eq.) was added to a room temperature solution of sulfonic acid (1 eq.) in dry acetone, followed by trimethylamine (1 eq.) dropwise. The solution was stirred vigorously and heated at 90° C. overnight. The reaction mixture was cooled to room temperature and, under nitrogen, 2-amino-1H-imidazole-4,5-dicarbonitrile (1.2 eq.), DMAP (0.25 eq.) and lithium carbonate (2 eq.) were added. The mixture was stirred vigorously and heated at 90° C. for 2 days. The reaction mixture was cooled down to room temperature. Distilled water was added, and the solution was extracted using dichloromethane. The combined organic layers were washed with water and acidic water, dried using MgSO4 and filtered. The solution was filtered on a diatomaceous earth filtration aid sold under the trademark CELITE® to eliminate inorganic residues. The organic solution was concentrated under reduced pressure until dryness. The solid residue was purified by silica gel chromatography using hexanes/ethyl acetate (1/1) as eluent. A crystalline yellow solid was isolated. The yellow solid was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

c) Compound A3

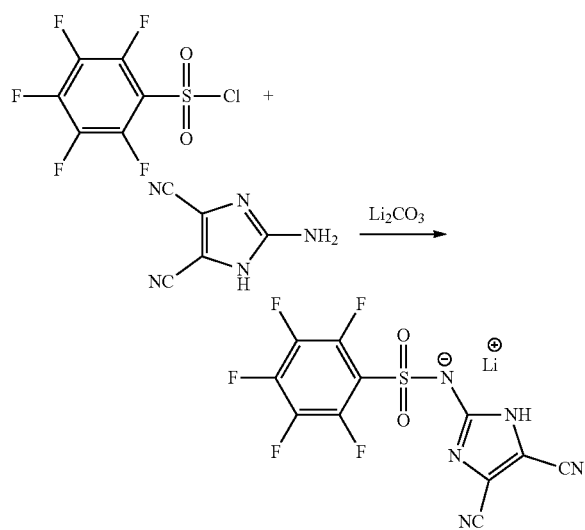

2-Amino-1H-imidazole-4,5-dicarbonitrile (1.1 eq), pentafluorosulfonylchloride (1 eq), lithium carbonate (2 eq) and N'N-dimethylaminopyridine (DMAP) (0.25 eq) were introduced in a Schlenk flask. The solids were degassed by vacuum-N2 cycles. Dry acetone (1M) was added and the suspension was vigorously stirred and heated under reflux. The reaction mixture was cooled down to room temperature. Distilled water was added, and the solution was extracted using dichloromethane. The combined organic layers were washed with water and acidic water, dried using MgSO4 and filtered. The solution was filtered on a diatomaceous earth filtration aid sold under the trademark CELITE® to eliminate inorganic residues. The organic solution was concentrated under reduced pressure until dryness. The solid residue was purified by silica gel chromatography using hexanes/ethyl acetate (1/1) as eluent. A crystalline yellow solid was isolated. The yellow solid was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

d) Compound A4

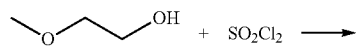

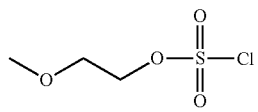

Step 1: A solution of 2-methoxyethan-1-ol in THF was added dropwise to a solution of sulfuryl chloride (1.2 eq) in THF at −75° C. The reaction mixture was warmed up to room temperature. The solution was concentrated until dryness under reduced pressure. The colorless oil obtained was used without purification.

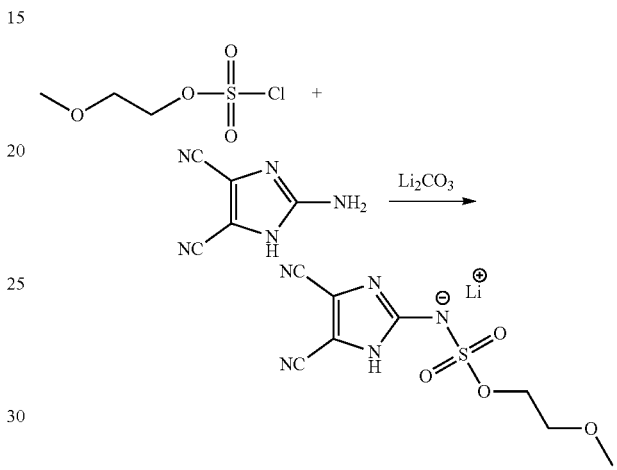

2-amino-1H-imidazole-4,5-dicarbonitrile (1.1 eq), 2-methoxyethan-1-sulfonylchloride (1 eq), lithium carbonate (2 eq) and N'N-dimethylaminopyridine (DMAP) (0.25 eq) were introduced in a Schlenk flask. The solids were degassed by vacuum-N2 cycles. Dry acetone (1M) was added and the suspension was stirred vigorously and heated under reflux overnight. The reaction mixture was cooled to room temperature. Distilled water was added and the resulting solution was extracted using dichloromethane. The organic layers were combined, washed with water and acidic water, dried on MgSO4 and filtered. The organic solution obtained was concentrated under reduced pressure until dryness. The resulting brown oil was purified by silica gel chromatography. A yellow oil was isolated. The resulting compound was converted to its lithium salt by dissolution in water and addition of lithium hydroxide. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

e) Compound A5

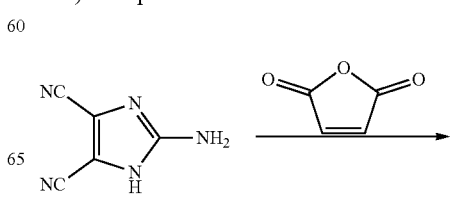

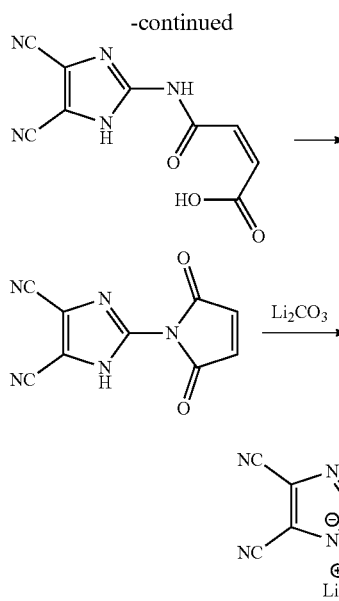

2-amino-1H-imidazole-4,5-dicarbonitrile and maleic anhydride were dissolved in 1,4-dioxane. The solution was heated at 150° C. during 10 hours by microwaves activation. The mixture was precipitated in cold diethyl ether and filtrated. The yellowish filtrate was evaporated, and a pale yellow highly hydroscopic solid was isolated. The solid was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

Example 2: Preparation of Compounds of Formula II a) Compound B1

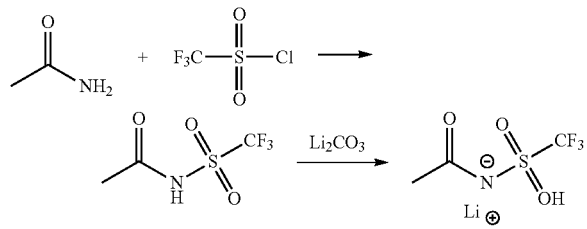

Acetamide (1.1 eq), trifluorosulfonylchloride (1 eq), lithium carbonate (2 eq) and N'N-dimethylaminopyridine (DMAP) (0.25 eq) were introduced in a Schlenk flask. The solids were degassed by vacuum-$N_2$ cycles. Dry acetone (1M) was added and the suspension was stirred vigorously and heated under reflux overnight. The reaction mixture was cooled down to room temperature. Distilled water was added, and the solution was extracted using dichloromethane. The combined organic phases were washed with water, dried on $MgSO_4$ and filtered. The organic solution was concentrated to dryness under reduced pressure. The crude oil was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

b) Compound B2

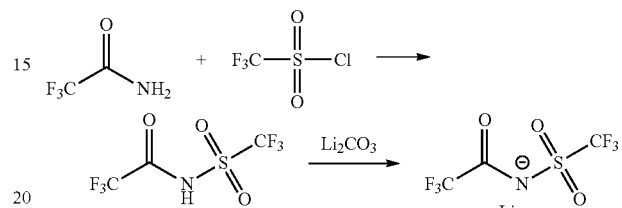

Trifluorocetamide (1.1 eq), trifluorosulfonylchloride (1 eq), lithium carbonate (2 eq) and N'N-dimethylaminopyridine (DMAP) (0.25 eq) were introduced in a Schlenk flask. The solids were degassed by vacuum-N2 cycles. Dry acetone (1M) was added and the suspension was stirred vigorously and heated under reflux overnight. The reaction mixture was cooled to room temperature. Distilled water was added, and the solution was extracted using dichloromethane. The organic layers were combined, washed with water, dried on MgSO4 and filtered. The organic solution was concentrated to dryness under reduced pressure. The crude oil was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduce pressure and dried in vacuum oven for 24 hours.

c) Compound B3

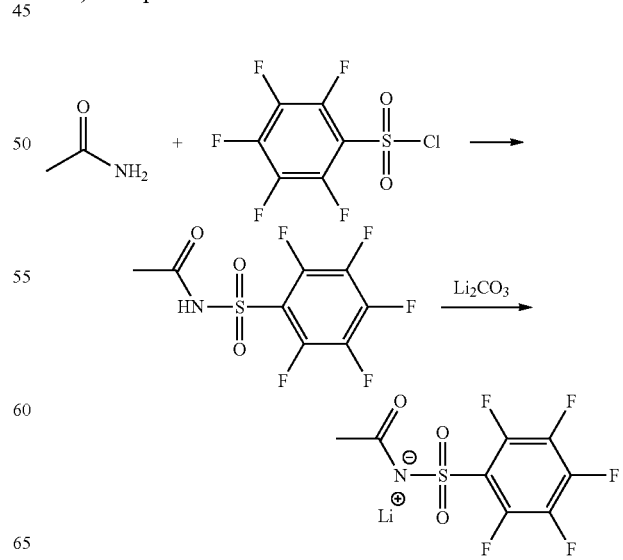

Acetamide (1.1 eq), pentafluorobenzenesulfonyl chloride (1 eq), lithium carbonate (2 eq) and N'N-dimethylaminopyridine (DMAP) (0.25 eq) were introduced in a Schlenk flask. The solids were degassed by vacuum-N2 cycles. Dry acetone (1M) was added and the suspension was stirred vigorously and heated under reflux overnight. The reaction mixture was cooled to room temperature, distilled water was added, and the solution was extracted using dichloromethane. The organic layers were combined, washed with water, dried on MgSO4 and filtered. The crude solid was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed through a diatomaceous earth filtration aid sold under the trademark CELITE® and the clear solution was concentrated under reduced pressure and dried in a vacuum oven for 24 hours.

d) Compound B4

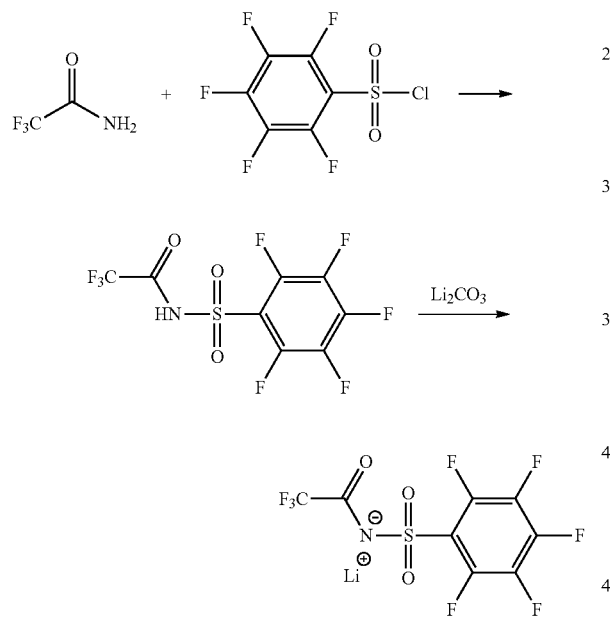

Trifluorocetamide (1.1 eq), pentafluorobenzenesulfonyl chloride (1 eq), lithium carbonate (2 eq) and N'N-dimethylaminopyridine (DMAP) (0.25 eq) were introduced in a Schlenk flask. The solids were degassed by vacuum-N2 cycles. Dry acetone (1M) was added and the suspension was stirred vigorously and heated under reflux overnight. The reaction mixture was cooled to room temperature, distilled water was added, and the solution was extracted using dichloromethane. The organic layers were combined, washed with water, dried on MgSO4 and filtered. The crude solid was then dissolved in water and monohydrated lithium hydroxide was added until a slight excess of base was detected using a pH paper. The solution was concentrated until dryness by reduced pressure distillation. The solid was suspended in diethyl carbonate (DEC) and stirred overnight at room temperature. The solution was passed on a diatomaceous earth filtration aid sold under the trademark CELITE® and the clear solution was concentrated under reduce pressure and dried in vacuum oven for 24 hours.

Example 3: Preparation of Compounds of Formula III

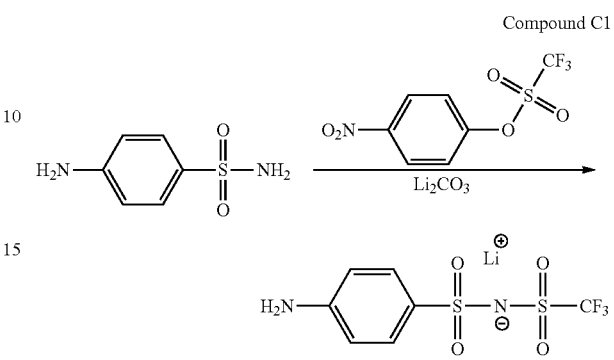

Step 1: Sulfanilamide, lithium carbonate (1 eq.) and 4-nitrophenyl trifluoromethanesulfonate were mixed and ground using a mortar and pestle. The molten mixture was stirred at 180° C. for one hour under nitrogen. Deionized water was added to the hot mixture under vigorous stirring. The insoluble suspended solid was removed by filtration. Water was removed under reduced pressure. The solid was washed with cold THF, ethyl acetate and a white solid was filtered. The yellow filtrate was evaporated under reduce pressure and the yellow solid was dried overnight at 40° C. under vacuum.

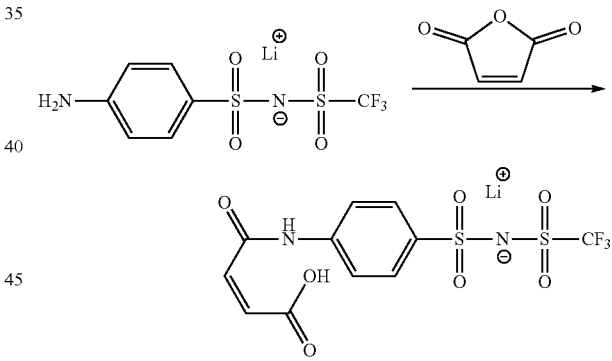

Step 2: A THF solution of the solid from step 1 was added to a solution of maleic anhydride in 1,4-dioxane and the resulting mixture was stirred at room temperature for 12 hours. The corresponding carboxylic acid was isolated as a white solid by filtration and was dried under vacuum at 60° C. for 4 hours.

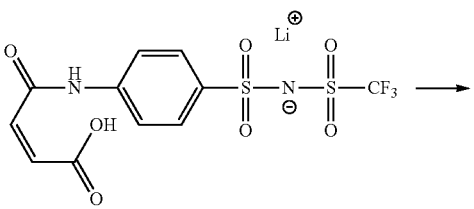

-continued

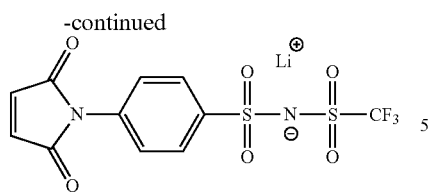

Step 3: A acetic anhydride solution of the carboxylic acid from step 2 and sodium acetate was heated at 70° C. for 3 hours. Then, the solution was poured into an excess of diethyl ether to complete the precipitation. The resulting precipitate was isolated by filtration and dried under vacuum at 60° C. overnight.

Example 4: Preparation of Compounds of Formulae IV and V a) Compound E2 (Free Form)

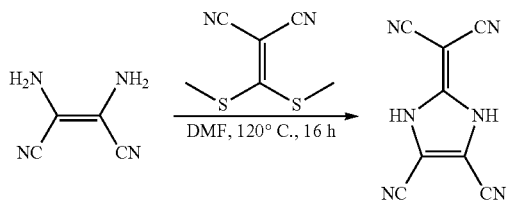

A solution of diaminomaleonitrile (1.0 g, 4.625 mmol) and anhydrous dimethylformamide (10 mL) is added to an inert reactor. The compound 2-[bis(methylthio)methylene]malononitrile (DM3) (0.787 g, 4.625 mmol) is added and the mixture stirred for 16 hours at 120° C. Solvents and volatile compounds are removed under vacuum. The resulting product is purified by silica-gel chromatography using a mixture of ethyl acetate and hexanes as eluent.

b) Compound D3 (Free Form)

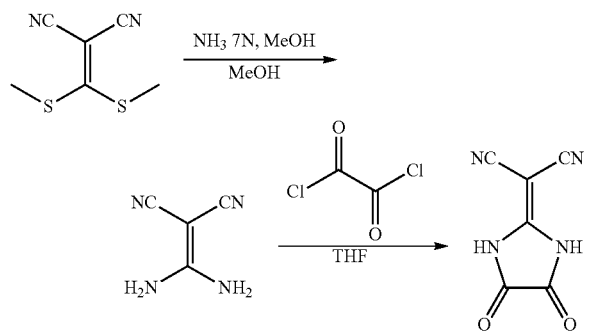

A solution of compound DM3 (0.500 g, 2.94 mmol) in methanol (50 mL) is inserted into an inert reactor (pressure bomb). Ammonia (0.500 g, 29.4 mmol) is added and the reaction mixture is stirred for 16 hours at 70° C. Solvent and volatile compounds are removed under vacuum. The compound obtained (DM3-NH$_2$) is used without further purification.

A solution of compound DM3-NH$_2$ (0.500 g, 4.63 mmol) in THF (50 mL) is introduced in an inert reactor. Oxalyl chloride (0.587 g, 4.63 mmol) is added and the reaction mixture is stirred for 16 hours at room temperature. The solvent and volatile compounds are removed under vacuum. The product is purified by recrystallization in alcohols.

c) Compound E4 (free form)

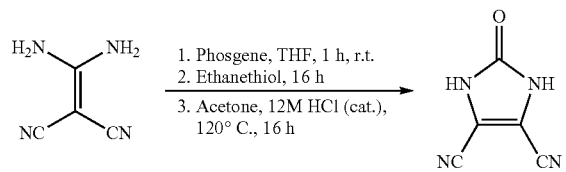 [SMILES: N#CC(C#N)=C(N)N ; N#Cc1[nH]c(=O)[nH]c1C#N]

A solution of diaminomaleonitrile (8.0 g, 74.0 mmol) in anhydrous tetrahydrofuran (250 mL) is introduced in an inert reactor and the solution is degassed. Phosgene (7.32 g, 74.0 mmol) is added and the mixture is stirred for 1 hour. Ethanethiol (14.9 g, 148.0 mmol) is then added and the mixture is stirred for another 16 h. The solvent and volatile compounds are removed under vacuum. Acetone (100 mL) and 5 drops of 12 M HCl are added and the mixture is heated for 16 h at 120° C. until a complete discoloration from orange to grey-white is observed. The product is a grey-white powder.

Example 5: Conductivity of Selected Salts

Conductivity measurements were carried out with a biologic conductivity meter (model MCS-10) using a platinum cell (type HTCC: parallel plates platinized platinum on glass holder). The salts were dried in a vacuum oven at 70° C. for one night prior to use, and PC/EMC/DMC (4/3/3) or distilled water were used as solvent. Solutions of LiCl (in water) or LiPF$_6$ (in PC/EMC/DMC) were used as references.

TABLE 1

Conductivity results

| Compound | Concentration (mol/L) | Conductivity (mS/cm) | Reference | Concentration (mol/L) | Conductivity (mS/cm) |
|---|---|---|---|---|---|
| A1 | 0.1M | 0.64 | LiPF$_6$ | 0.1M | 2.96 |
| A2 | 0.3M | 0.63 | LiPF$_6$ | 0.3M | 6.78 |
| A5 | 0.1M | 0.04 | LiPF$_6$ | 0.1M | 2.96 |
| A5 | 0.1M | 21.66 | LiCl | 0.1M | 9.75 |
| E2* | 0.1M | 9.71 | LiCl | 0.1M | 9.75 |

*In its di-lithium salt form.

Numerous modifications could be made to any of the embodiments described above without departing from the scope of the present invention. Any references, patents or scientific literature documents referred to in this application are incorporated herein by reference in their entirety for all purposes.

The invention claimed is:
1. A compound as defined in Formula I:

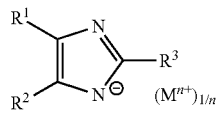

Formula I wherein,
R$^1$ and R$^2$ are independently selected from H, F, CN, NO$_2$, and optionally substituted alkyl;

R³ is selected from —NHSO₂R⁴, —NHSO₂OR⁴, —SO₂NHSO₂R⁴, —SO₂NHSO₂OR⁴ and an optionally substituted non-aromatic heterocycle having 5 or 6 cycle atoms linked through a nitrogen atom of the non-aromatic heterocycle;
R⁴ is selected from fluorine, optionally substituted $C_{1-6}$alkyl, and optionally substituted $C_6$aryl; and
$(M^{n+})_{1/n}$ is a metal cation, wherein M is an alkali metal or alkaline earth metal and n is 1 or 2;
or a tautomer thereof.

2. The compound of claim 1, wherein M is Li, Na, or K, and n is 1.

3. The compound of claim 1, wherein M is Li and n is 1.

4. The compound of claim 1, wherein said compound is selected from:

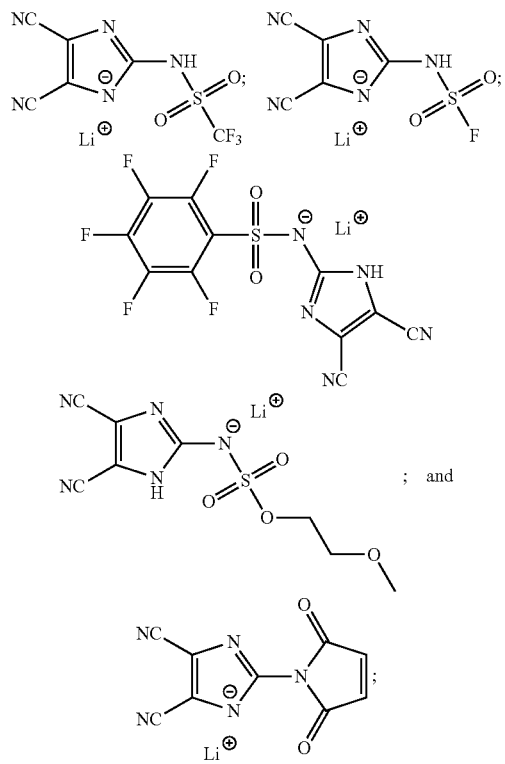

or a tautomer thereof.

5. The compound of claim 1, wherein at least one of R¹ and R² is CN.

6. The compound of claim 5, wherein both of R¹ and R² are CN.

7. The compound of claim 1, wherein R³ is NHSO₂R⁴, NHSO₂OR⁴ or a non-aromatic heterocycle having 5 or 6 cycle atoms linked through the nitrogen atom of the non-aromatic heterocycle.

8. The compound of claim 7, wherein R⁴ is a $C_{1-6}$alkyl substituted with at least one of fluorine and alkoxy or a $C_6$aryl substituted with at least one fluorine atom.

9. Electrode material comprising a compound as defined in claim 1 as an additive and at least one electrochemically active material.

10. An electrochemical cell comprising an electrolyte, an electrode and a counter-electrode, wherein at least one of the electrode or counter-electrode comprises an electrode material as defined in claim 9.

11. An electrolyte composition comprising a compound as defined in claim 1.

12. The electrolyte composition of claim 11, further comprising a compatible organic or aqueous solvent.

13. The electrolyte composition of claim 11, further comprising a compatible solvating polymer.

14. The electrolyte composition of claim 11, wherein said compound is selected from:

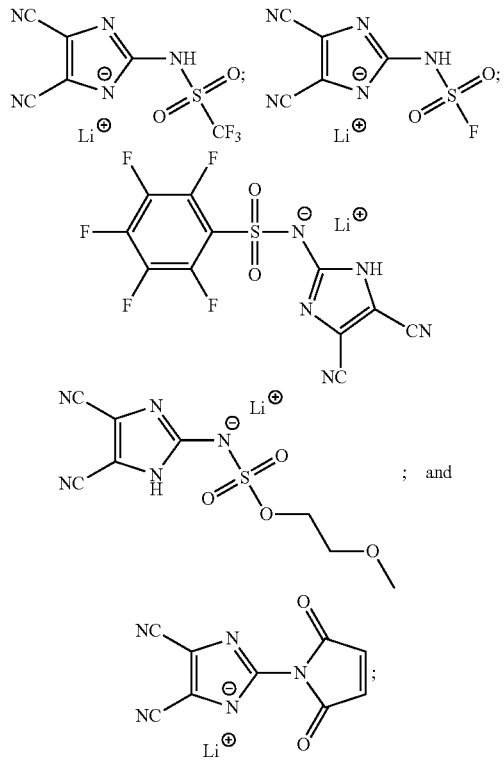

or a tautomer thereof.

15. An electrochemical cell comprising an electrolyte, an electrode and a counter-electrode, wherein the electrolyte comprises an electrolyte composition as defined in claim 11.

16. The electrochemical cell of claim 15, wherein said electrochemical cell is a battery, an electrochromic device, or a capacitor.

17. The electrochemical cell of claim 16, wherein said electrochemical cell is a lithium or lithium-ion battery.

18. A compound as defined in Formula I:

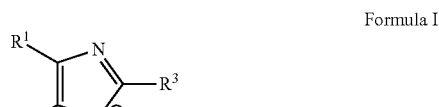

wherein,
R¹ and R² are independently selected from H, F, CN, NO₂, and optionally substituted alkyl;
R³ is selected from —NHSO₂R⁴, —NHSO₂OR⁴, —SO₂NHSO₂R⁴, —SO₂NHSO₂OR⁴ and an optionally substituted non-aromatic heterocycle having 5 or 6 cycle atoms linked through a nitrogen atom;
R⁴ is selected from fluorine, optionally substituted $C_{1-6}$alkyl, and optionally substituted $C_6$aryl; and $(M^{n+})_{1/n}$ is a metal cation, wherein M is lithium and n is 1;
or a tautomer thereof.

19. A compound as defined in Formula I:

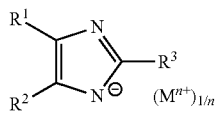

Formula I wherein,
$R^1$ and $R^2$ are independently selected from H, F, CN, $NO_2$, and optionally substituted alkyl, wherein at least one of $R^1$ and $R^2$ is CN;
$R^3$ is selected from —$NHSO_2R^4$, —$NHSO_2OR^4$, —$SO_2NHSO_2R^4$, —$SO_2NHSO_2OR^4$ and an optionally substituted non-aromatic heterocycle having 5 or 6 cycle atoms linked through a nitrogen atom;
$R^4$ is selected from fluorine, optionally substituted $C_{1-6}$alkyl, and optionally substituted $C_6$aryl; and
$(M^{n+})_{1/n}$ is a metal cation, wherein M is an alkali metal or alkaline earth metal and n is 1 or 2;
or a tautomer thereof.

20. A compound as defined in Formula I:

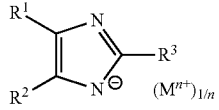

Formula I wherein,
$R^1$ and $R^2$ are CN;
$R^3$ is selected from —$NHSO_2R^4$, —$NHSO_2OR^4$, —$SO_2NHSO_2R^4$, —$SO_2NHSO_2OR^4$ and an optionally substituted non-aromatic heterocycle having 5 or 6 cycle atoms linked through a nitrogen atom;
$R^4$ is selected from fluorine, optionally substituted $C_{1-6}$alkyl, and optionally substituted $C_6$aryl; and
$(M^{n+})_{1/n}$ is a metal cation, wherein M is an alkali metal or alkaline earth metal and n is 1 or 2;
or a tautomer thereof.

21. An electrolyte composition or electrode material comprising a compound as defined in Formula I:

Formula I wherein,
$R^1$ and $R^2$ are independently selected from H, F, CN, $NO_2$, and optionally substituted alkyl;
$R^3$ is selected from —$NHSO_2R^4$, —$NHSO_2OR^4$, —$SO_2NHSO_2R^4$, —$SO_2NHSO_2OR^4$ and an optionally substituted non-aromatic heterocycle having 5 or 6 cycle atoms linked through a nitrogen atom;
$R^4$ is selected from fluorine, optionally substituted $C_{1-6}$alkyl, and optionally substituted $C_6$aryl; and
$(M^{n+})_{1/n}$ is a metal cation, wherein M is an alkali metal or alkaline earth metal and n is 1 or 2;
or a tautomer thereof.

22. An electrochemical cell comprising an electrolyte, an electrode and a counter-electrode, wherein the electrolyte comprises the electrolyte composition as defined in claim 21 or at least one of the electrode or counter-electrode comprises the electrode material as defined in claim 21.

* * * * *